United States Patent
Pardonge

(10) Patent No.: US 7,594,596 B2
(45) Date of Patent: Sep. 29, 2009

(54) FLUID PRODUCT DISPENSING VALVE AND FLUID PRODUCT DISPENSING DEVICE COMPRISING SAME

(75) Inventor: Jean-Marc Pardonge, Saint-Ouen (FR)

(73) Assignee: Valois S.A.S., Le Neubourg (FR)

( * ) Notice: Subject to any disclaimer, the term of this patent is extended or adjusted under 35 U.S.C. 154(b) by 568 days.

(21) Appl. No.: 10/527,197

(22) PCT Filed: Jul. 10, 2003

(86) PCT No.: PCT/FR03/02180

§ 371 (c)(1),
(2), (4) Date: Mar. 10, 2005

(87) PCT Pub. No.: WO2004/024220

PCT Pub. Date: Mar. 25, 2004

(65) Prior Publication Data

US 2005/0279778 A1    Dec. 22, 2005

(30) Foreign Application Priority Data

Sep. 10, 2002    (FR)    .................... 02 11176

(51) Int. Cl.
*B65D 83/00*    (2006.01)
*F28F 1/14*    (2006.01)
*A61M 11/00*    (2006.01)
*F16K 49/00*    (2006.01)

(52) U.S. Cl. ............ 222/402.1; 222/146.6; 222/402.22; 222/146.3; 165/184; 128/200.23; 128/203.14; 137/338

(58) Field of Classification Search ................. 251/368; 128/200.23, 203.14; 165/184; 222/402.1, 222/402.2, 402.22, 402.23, 146.1, 146.2, 222/146.3, 146.4, 146.6, 162; 137/338, 339
See application file for complete search history.

(56) References Cited

U.S. PATENT DOCUMENTS

| 3,075,542 A | * | 1/1963 | Diesing ...................... 137/338 |
| 3,184,115 A | | 5/1965 | Meshberg |
| 3,236,420 A | | 2/1966 | Walter |
| 3,292,823 A | | 12/1966 | Weidman et al. |
| 3,338,476 A | * | 8/1967 | Marcoux ................. 222/146.3 |
| 3,347,422 A | * | 10/1967 | Mead et al. ............... 222/146.3 |
| 3,476,293 A | * | 11/1969 | Marcoux ................. 222/146.3 |
| 3,783,511 A | * | 1/1974 | Pass ............................. 30/41 |
| 5,007,556 A | * | 4/1991 | Lover ..................... 222/386.5 |
| 6,510,969 B2 | * | 1/2003 | Di Giovanni et al. .... 222/402.2 |
| 6,655,552 B2 | * | 12/2003 | Aiken et al. ............. 222/146.3 |

FOREIGN PATENT DOCUMENTS

| EP | 0 308 524 A | 3/1989 |
| EP | 0 534 749 A | 3/1993 |
| FR | 1 340 404 A | 10/1963 |
| JP | 53 096516 A | 8/1978 |
| WO | WO 01 89616 A | 11/2001 |
| WO | WO 01 96210 A | 12/2001 |
| WO | WO 02 49569 A | 6/2002 |

* cited by examiner

Primary Examiner—Kevin P Shaver
Assistant Examiner—Stephanie E Tyler
(74) Attorney, Agent, or Firm—Sughrue Mion, PLLC

(57) ABSTRACT

A fluid-dispenser valve (10) comprising a valve body (11), and a valve member (12) slidable in said valve body (11) between a rest position and a dispensing position, said valve (10) including temperature regulator means (12, 20) for limiting cooling of the valve member (12) while the fluid is being dispensed.

19 Claims, 3 Drawing Sheets

FLUID PRODUCT DISPENSING VALVE AND FLUID PRODUCT DISPENSING DEVICE COMPRISING SAME

The present invention relates to a fluid-dispenser valve and to a fluid dispenser device including such a valve.

Fluid-dispenser valves are well known in the prior art. They generally comprise a valve body in which a valve member slides between a rest position and a dispensing position in which the fluid is dispensed. The fluid is generally dispensed by means of a propellant gas, and that type of valve is commonly referred to as an "aerosol valve". With metering valves, the valve body includes a valve chamber which precisely defines the volume of fluid dispensed each time the valve is actuated.

In conventional manner, metering valves generally dispense dose volumes lying in the range 50 microliters (µl) to 100 µl. In this event, the time taken to dispense a dose is relatively short. However, in metering valves for dispensing much larger volumes, e.g. volumes greater than 500 µl, the very nature of the aerosol fluid can lead to problems with valve operation. Thus, since the time taken to dispense a dose is relatively long, the valves which dispense very large doses are subjected to intense cooling as a result of the nature of the aerosol fluid to be dispensed and the dispensing method. In particular, the expansion of the propellant gas causes such cooling. In some circumstances, cooling can lead to the valve malfunctioning, in particular by blocking the outlet channels, particularly at the valve member.

An object of the present invention is to provide a fluid-dispenser valve which does not have the above-mentioned drawbacks.

More particularly, an object of the present invention is to provide a fluid-dispenser valve which functions in safe and reliable manner, regardless of the volume of fluid dispensed while it is being actuated.

Another object of the present invention is to provide such a fluid-dispenser valve that is simple and inexpensive to manufacture and to assemble.

Another object of the present invention is to provide a fluid dispenser device including such a valve.

The present invention therefore provides a fluid-dispenser valve comprising a valve body, and a valve member slidable in said valve body between a rest position and a dispensing position, said valve being characterized in that it includes temperature regulator means for limiting cooling of the valve member while the fluid is being dispensed.

Advantageously, said temperature regulator means comprise a valve member made, at least in part, of a thermally-conductive material.

Advantageously, said valve member includes an inner portion, slidable inside the valve body, and made of a first material, and an outer portion, extending, at least in part, outside the valve body, and made of a second material that is thermally conductive, said inner and outer portions being secured to each other, in particular by overmolding.

Advantageously, said temperature regulator means comprise a head co-operating with said valve member, said head being made of a thermally-conductive material.

Advantageously, said temperature regulator means comprise cooling plates co-operating with said valve member.

In a first embodiment, said plates are disposed around said valve member.

In a second embodiment, said plates are disposed in a head co-operating with said valve member.

Advantageously, said plates extend approximately parallel to one another, and substantially transversely to the central axis of said valve member.

Advantageously, said plates are made of a thermally-conductive material.

Advantageously, said thermally-conductive material is a metal, in particular aluminum.

Advantageously, the fluid-dispenser valve functions with a propellant gas so as to dispense the fluid.

Advantageously, said propellant gas comprises gases of the HFA-134a or HFA-227 type.

Advantageously, said valve is a metering valve, said valve body including a valve chamber defining a volume of fluid to be dispensed each time the valve is actuated.

Advantageously, said volume of fluid dispensed at each actuation is greater than 500 µl.

The present invention also provides a fluid dispenser device comprising a fluid reservoir and a valve as defined above.

Advantageously, the fluid dispenser device includes a dispenser head mounted on the valve member of said valve.

Advantageously, said dispenser head, and in particular the portion co-operating with the valve member, includes said temperature regulator means.

Other characteristics and advantages of the present invention appear more clearly from the following detailed description, given by way of non-limiting examples, and with reference to the accompanying drawing, and in which.

Figure 1:
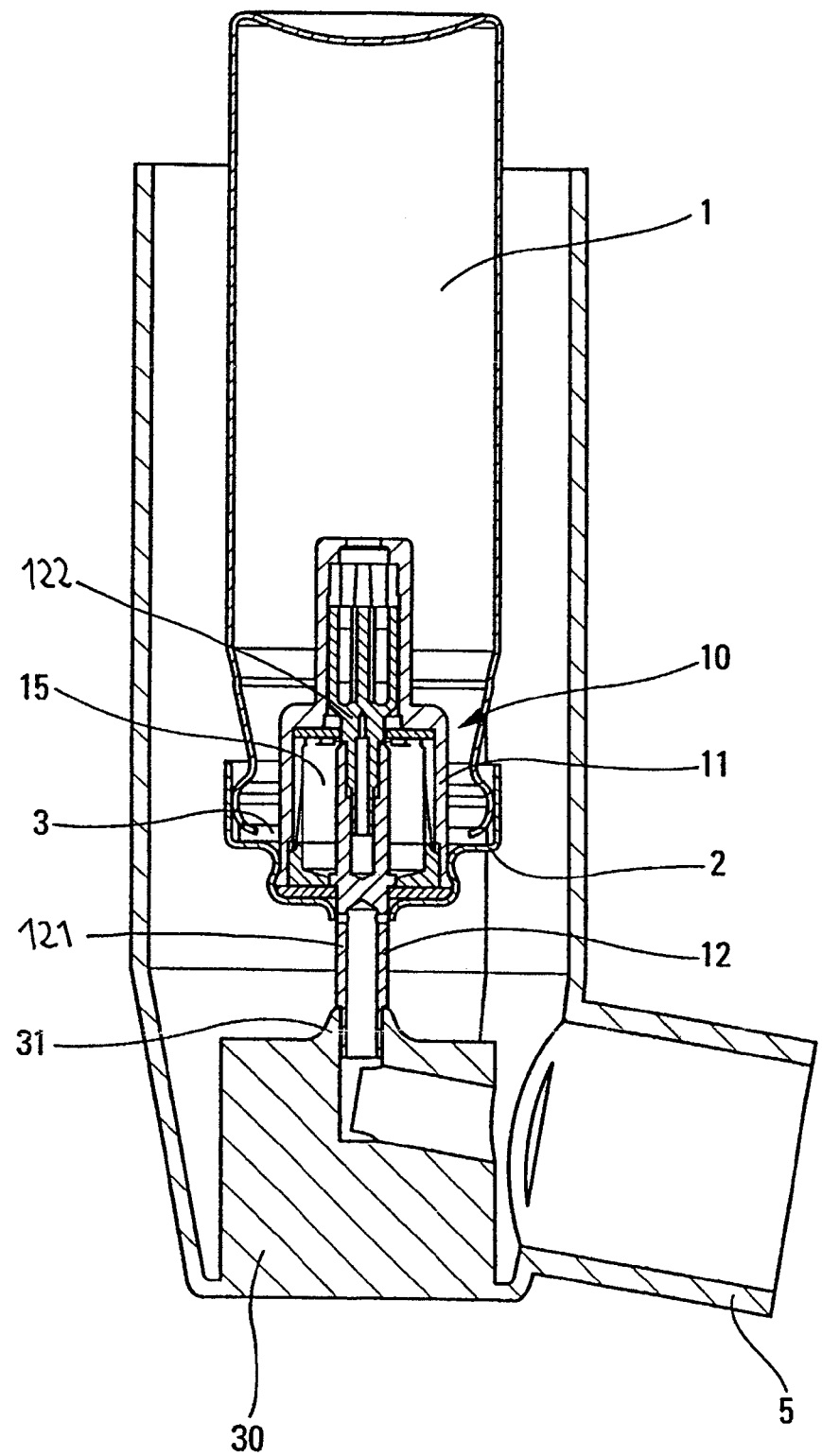
FIG. 1 is a diagrammatic section view of a fluid dispenser device including a dispenser valve constituting a first embodiment of the present invention.

With reference to the figures, a fluid dispenser device comprises a reservoir 1 on which a valve 10 is mounted by means of a ring 2, preferably a clamping ring or cap as shown in the figures. A neck gasket 3 is generally interposed between the neck of the reservoir 1 and said ring 2. The reservoir 1 contains a fluid, with a fraction of the fluid being dispensed each time the valve 10 is actuated.

The valve is preferably a metering valve, and includes a valve body 11 enclosing a valve chamber 15 that defines the volume of each dose of fluid dispensed each time the valve 10 is actuated. A valve member 12 is slidably mounted in said valve body 11 between a rest position, shown in the figures, and an actuated position, into which said valve member 12 is driven inside said valve body 11 so as to dispense the dose of fluid contained in the valve chamber 15. The fluid is dispensed by means of a propellant gas, preferably of the HFA-134a or HFA-227 type, which are gases that are not harmful to the environment. A dispenser head 30 is generally assembled on the valve member 12 so as to connect the outlet orifice of said valve member 12 to a dispenser orifice of the fluid dispenser member. In the embodiment shown in the figures, the dispenser head 30 connects the valve member 12 to a mouthpiece 5 of the device. Naturally, the present invention is not limited to the embodiments shown in FIGS. 1 to 3, and the various component parts of the device (the reservoir, the valve, the fastening ring, the dispenser head, the body of the device, etc.) can be made in any appropriate way.

In the invention, the valve 10 includes temperature regulator means for limiting cooling of the valve member 12 while the valve 10 is being actuated, and thus while the fluid is being dispensed. As explained above, the problem of intense cooling occurs in particular with valves for dispensing large volumes on each actuation, e.g. volumes that can be as great as 600 μl. However, the present invention is not limited exclusively to valves that dispense large volumes, but extends more generally to any valve in which a problem exists with regard to valve operation and reliability as a result of significant cooling during dispensing.

FIG. 1 shows a first embodiment of the present invention. In this first embodiment, the valve member 12 is made of a material having a high co-efficient of thermal conductivity. The material can be a metal, in particular aluminum. Naturally, any other material having a high co-efficient of thermal conductivity could be used. As a result of making the valve member 12 from such a thermally-conductive material, its cooling time can be increased, and thus its cooling can be limited. This prevents the outlet channels of the valve, and in particular of the valve member, from becoming blocked during dispensing.

In a variant, only part of the valve member 12 need be made of a thermally-conductive material, such as aluminum. For example, the valve member could be made of a thermally-conductive material on that part only of its outer portion that extends outside the valve body. The outer portion (121) could be secured, preferably by overmolding, on an inner portion (122) of the valve member that is slidable inside the valve body, which could be made of a conventional synthetic material. Overmolding guarantees perfect sealing. This embodiment makes it possible to limit contact between the active fluid and the metal, and it can be adapted easily on existing valve members.

In a variant, or in complementary manner, the head 30 could be made of a thermally-conductive material, e.g. of aluminum. Advantageously, when the head 30 is made integrally as a single piece with the dispenser body, a result of making the piece of thermally-conductive material causes the heat from the hand of the user to be transmitted thereto when said user holds the dispenser. This makes it possible to limit cooling of the valve member still further.

Figure 2:
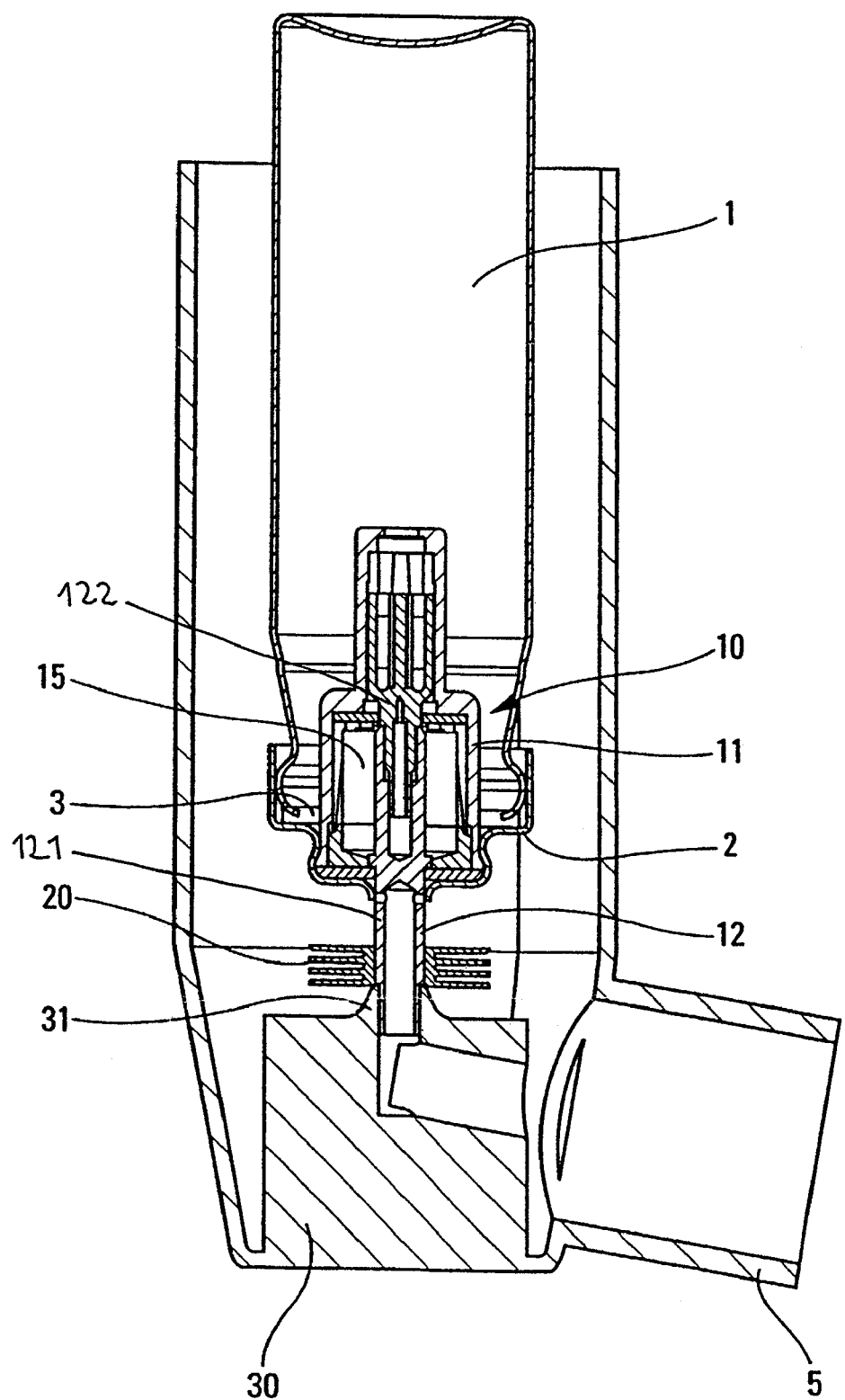
FIG. 2 is a view similar to the view in FIG. 1, constituting a second embodiment of the present invention.

FIG. 2 shows another embodiment of the present invention, in which the temperature regulator means include cooling plates 20. In the embodiment in FIG. 2, the cooling plates 20 are disposed around the valve member 12 and extend approximately transversely to the central axis of said valve member 12. FIG. 2 shows four plates extending approximately parallel to one another, each plate being formed by a disk having a central hole through which the valve member 12 passes. Naturally, the cooling plates 20 could be of any desired number, and their shape could also be different, the purpose being to obtain a large surface area so as to enable heat to be conducted in an amount that is large and sufficient to limit cooling, and thus prevent the valve from malfunctioning. The use of cooling plates 20 around the valve member 12 makes it possible to use conventional valves having valve members made of plastics material. The cooling plates 20 can also be made of a plastics material. In a variant, in order to conduct still more heat, the cooling plates 20 can be made of a material having a high co-efficient of thermal conductivity, e.g. a metal, and in particular aluminum. If necessary, the metal cooling plates can also be associated with a valve member 12 that is itself made of metal, so as to maximize heat conduction.

Figure 3:
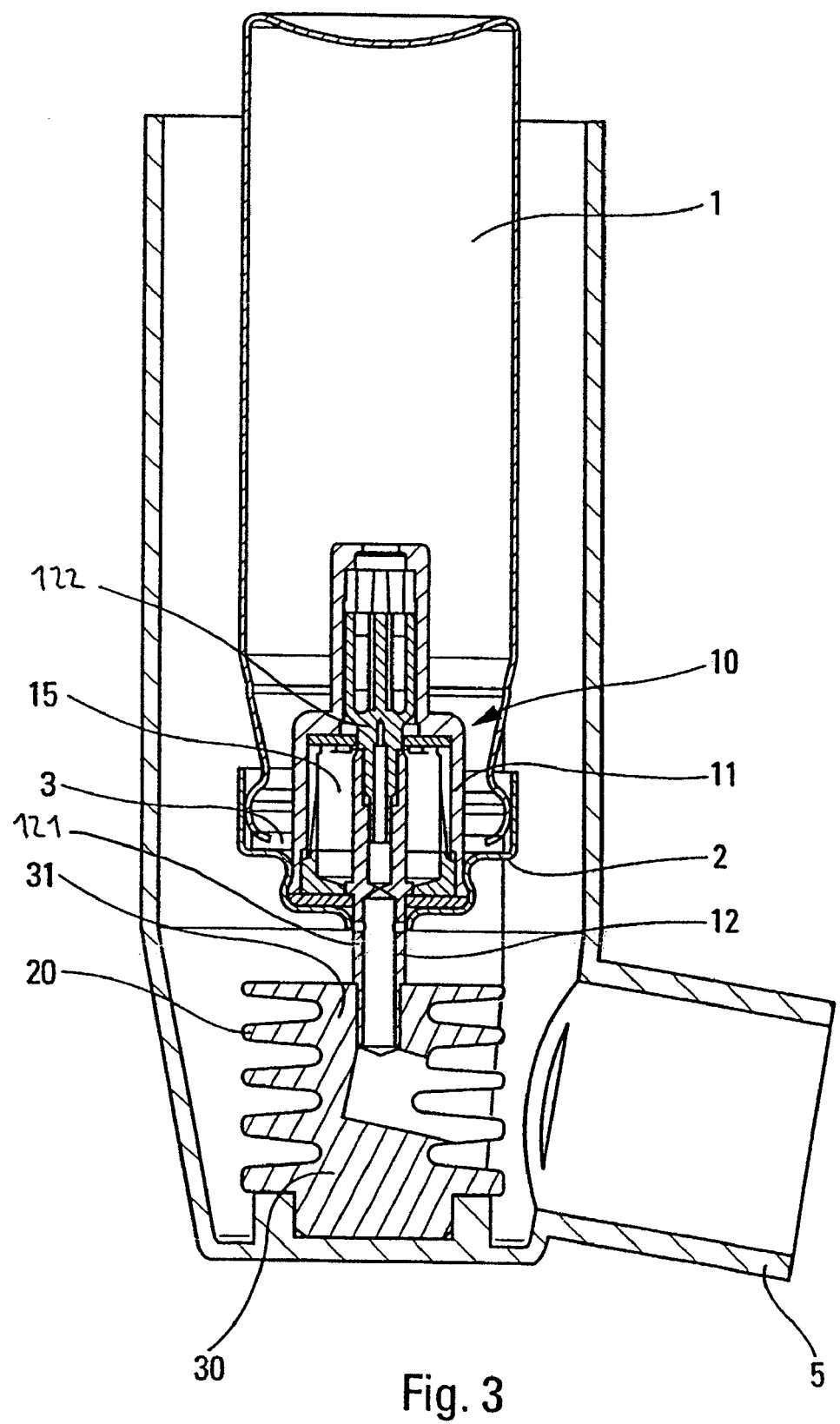
FIG. 3 is a view similar to the views in FIGS. 1 and 2, showing a third embodiment of the present invention.

FIG. 3 shows another embodiment of the present invention. In this third embodiment, the cooling plates 20 are not formed on the valve member 12, but in the dispenser head 30 which co-operates with said valve member 12. It is more particularly on the portion 31 assembled on the valve member 12, that it is advantageous to form temperature regulator means, e.g. cooling plates 20. Naturally, the cooling plates 20 could be of any number, and they could extend over the entire head 30, as shown in FIG. 3. Once again, the valve member could be made of a plastics material, as could the plates 20 of the head 30. If necessary, the valve member 12 and/or said plates 20 can be made of a material having a high co-efficient of thermal conductivity, in particular they can be made of metal, such as aluminum.

Naturally, it is quite possible to envisage combining the various embodiments described above, and therefore using a valve member that is thermally conductive, at least in part, and temperature regulator means 20 both around the valve member 12 and in the dispenser head 30, if necessary. The essential purpose of the present invention is to limit cooling while the fluid is being dispensed, so as to prevent the valve from malfunctioning, in particular by becoming blocked, which can occur when the valve dispenses very large volumes, as explained above.

Although the present invention is described above with reference to the particular embodiments shown in the figures, it is naturally not limited to the embodiments shown and described above, but on the contrary, it encompasses any modifications which could be applied thereto by a person skilled in the art, without going beyond the ambit defined by the accompanying claims. For example, it is possible to envisage providing heater means, or the like, at or in the vicinity of the valve member. Other types of temperature regulator means could also be envisaged.

The invention claimed is:

1. A fluid-dispenser valve (10) comprising a valve body (11), and a valve member (12) slidable in said valve body (11) between a rest position and a dispensing position, said valve (10) being characterized in that it includes temperature regulator means (12, 20) for limiting cooling of the valve member (12) while the fluid is being dispensed, said temperature regulator means comprising the valve member (12), and said valve member (12) including an inner portion, slidable inside the valve body (11), and made of a first synthetic material, and an outer portion, extending, at least in part, outside the valve body, and made of a second material that is thermally conductive, said inner and outer portions being secured to each other.

2. A valve according to claim 1, in which said temperature regulator means further comprise a head (30) co-operating with said valve member (12), said head (30) being made of a thermally-conductive material.

3. A valve according to claim 1, in which said temperature regulator means further comprise cooling plates (20) co-operating with said valve member (12).

4. A valve according to claim 3, in which said plates (20) are disposed around said valve member (12).

5. A valve according to claim 3, in which said plates (20) are disposed in a head (30) co-operating with said valve member (12).

6. A valve according to claim 3, in which said plates (20) extend approximately parallel to one another, and substantially transversely to the central axis of said valve member (12).

7. A valve according to claim 3, in which said plates (20) are made of a thermally-conductive material.

8. A valve according to claim 1, in which said thermally-conductive material is a metal.

9. A valve according to claim 1, operating with a propellant gas so as to dispense the fluid.

10. A valve according to claim 9, in which said propellant gas comprises gases of the HFA-134a or HFA-227 type.

11. A valve according to claim 1, in which said valve (10) is a metering valve, said valve body (11) including a valve chamber (15) defining a volume of fluid to be dispensed each time the valve (10) is actuated.

12. A valve according to claim 11, in which said volume of fluid dispensed at each actuation is greater than 500 µl.

13. A fluid dispenser device comprising a fluid reservoir (1), said device being characterized in that it further comprises a valve (10) according to claim 1.

14. A device according to claim 13, including a dispenser head (30) mounted on the valve member (12) of said valve (10).

15. A device according to claim 14, in which said dispenser head (30) includes said temperature regulator means (20).

16. The valve according to claim 1, wherein the inner and outer portions are secured to each other by overmolding.

17. The valve according to claim 1, in which said thermally-conductive material is aluminum.

18. The device according to claim 14, in which a portion of the dispenser head that co-operates with the valve member (12) includes the temperature regulator means.

19. A fluid-dispenser valve, comprising:
a valve body, and
a tubular valve member comprising an inner portion slidable inside the valve body between a rest position and a dispensing position and an outer portion extending, at least in part, outside the valve body, and
wherein the inner portion is made, at least in part, of a synthetic material and the outer portion is made, at least in part, of a thermally conductive material; and
wherein the inner and outer portions are secured to each other; and
wherein the fluid dispenser valve further comprises cooling plate fins thermally coupled to the valve member.

* * * * *